(12) United States Patent
Chassot et al.

(10) Patent No.: US 7,074,243 B2
(45) Date of Patent: Jul. 11, 2006

(54) N-BENZYL-M-PHENYLENEDIAMINE DERIVATIVES AND DYES CONTAINING SAID COMPOUNDS

(75) Inventors: Laurent Chassot, Praroman (CH); Hans-Juergen Braun, Ueberstorf (CH)

(73) Assignee: WELLA AG, Darmstadt (DE)

( * ) Notice: Subject to any disclaimer, the term of this patent is extended or adjusted under 35 U.S.C. 154(b) by 268 days.

(21) Appl. No.: 10/333,045

(22) PCT Filed: Feb. 2, 2002

(86) PCT No.: PCT/EP02/01087

§ 371 (c)(1),
(2), (4) Date: Jan. 15, 2003

(87) PCT Pub. No.: WO02/096854

PCT Pub. Date: Dec. 1, 2002

(65) Prior Publication Data

US 2003/0182735 A1    Oct. 2, 2003

(30) Foreign Application Priority Data

May 25, 2001 (DE) ................ 101 25 451

(51) Int. Cl.
*A61K 7/13* (2006.01)

(52) U.S. Cl. ............ 8/405; 8/406; 8/410; 8/411; 8/412; 8/416; 564/305; 564/306; 564/336

(58) Field of Classification Search .......... 8/405, 8/406, 410, 411, 412, 416; 564/305, 306, 564/336

See application file for complete search history.

(56) References Cited

FOREIGN PATENT DOCUMENTS

| DE | 128 754 C | 2/1902 |
|---|---|---|
| DE | 141 297 C | 4/1903 |
| DE | 24 49 101 A | 4/1975 |
| DE | 29 34 330 A1 | 3/1981 |
| DE | 199 61 274 C | 2/2001 |
| DE | 101 03 160 A | 11/2001 |
| DE | 10103160 A1 * | 11/2001 |
| EP | 0 024 660 A | 3/1981 |
| EP | 1 116 711 A | 7/2001 |
| WO | 97 49770 A | 12/1997 |

OTHER PUBLICATIONS

Database XP 002198131 & Acta Pol. Pharm vol. 21, 1964, p. 488, 490 and 491.*
Database Crossfire Beilstein 'Online! Beilstein Institute Zur Foerderung Der Chemischen Wisenschaften, Frankfurt Am Main, & Acta Pol. Pharm., Bd. 21, 1964, pp. 488,490,491.
"Protective Groups" In Organic Synthesis, Chapter 7, Wiley Interscience, 1991, pp. 494-653.

* cited by examiner

*Primary Examiner*—Eisa Elhilo
(74) *Attorney, Agent, or Firm*—Michael J. Striker

(57) ABSTRACT

N-benzyl-m-phenylenediamine derivatives of general formula (I) or the physiologically tolerated, water-soluble salts thereof

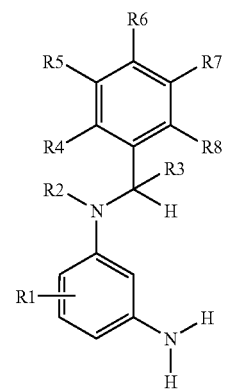

(I)

and dyeing agents for keratin fibers containing these compounds.

11 Claims, No Drawings

N-BENZYL-M-PHENYLENEDIAMINE DERIVATIVES AND DYES CONTAINING SAID COMPOUNDS

BACKGROUND OF THE INVENTION

1. Field of the Invention

The invention relates to novel N-benzyl-m-phenylenediamine derivatives and to agents for dyeing keratin fibers containing these compounds.

2. Description of the Related Art

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2-(2,5-diaminophenyl)ethyl alcohol, 1-(2,5-diaminophenyl)ethyl alcohol, p-aminophenol, 1,4-diaminobenzene and 4,5-diamino-1-(2-hydroxyethyl)pyrazole, whereas suitable couplers are, for example, resorcinol, 2-methylresorcinol, 1-naphthol, 3-aminophenol, 2-amino-4-(2'-hydroxyethyl)aminoanisole, 1,3-diamino-4-(2'-hydroxyethoxy)benzene and 2,4-diamino-5-fluorotoluene.

The oxidation dyes used for dyeing human hair must meet numerous requirements in addition to that of being able to produce colorations of the desired intensity. For example, these dyes must be harmless from a toxicological and dermatological standpoint, and the hair colorations obtained must have good light fastness, resistance to permanent waving, acid fastness and rubbing fastness. In any case, however, in the absence of exposure to light, rubbing and chemicals, such colorations must remain stable over a period of at least 4 to 6 weeks. Moreover, by combining appropriate developers and couplers, it must be possible to create a wide range of different color shades.

Attempts have already been made to improve the properties of m-phenylenediamines by introduction of substituents, In this regards the reader is referred to German Unexamined Patent Application DE 29 34 330 which, among other things, describes special N-substituted m-phenylenediamines as couplers. With the currently known dyeing agents, however, it is not possible to meet the requirements placed on dyeing agents in all respects, Hence, the need continued to exist for novel couplers that would meet the aforesaid requirements to a particularly high degree.

Surprisingly, we have now found that by use of N-benzyl-m-phenylenediamine derivatives of general formula (I), intense, stable purple to blue color shades can be obtained.

The object of the present invention are therefore N-benzyl-m-phenylenediamine derivatives of general formula (I) or physiologically tolerated, water-soluble salts thereof (I)

wherein

R1 denotes a halogen atom (F, Cl, Br, I), a $C_1$–$C_4$-alkoxy group, a $C_1$–$C_4$-fluoroalkoxy group, a ($C_1$–$C_4$-alkyl)sulfamido-($C_2$–$C_4$-alkoxy) group, a ($C_1$–$C_4$-alkyl)sulfonyl-($C_2$–$C_4$-alkoxy) group, a $C_2$–$C_4$-hydroxyalkoxy group, a $C_3$–$C_4$-dihydroxyalkoxy group, a $C_1$–$C_6$-alkyl group, a $C_1$–$C_4$-alkylthioether group, a $C_2$–$C_4$-aminocarbonylalkoxy group, an aminoalkyl group, a trifluoromethyl group, an —Si($CH_3$)$_3$ group, a $C_1$–$C_4$-hydroxyalkyl group or a $C_3$–$C_4$-dihydroxyalkyl group;

R2 and R3 independently of each other denote hydrogen or a ($C_1$–$C_4$)-alkyl group;

R4, R5, R6, R7 and R8 independently of each other denote hydrogen, a halogen atom (F, Cl, Br, I), a hydroxyl group, a ($C_1$–$C_4$)-alkoxy group, a hydroxy-($C_2$–$C_4$)-alkoxy group, a ($C_1$–$C_6$)-alkyl group, a ($C_1$–$C_4$)-alkylthioether group, a mercapto group, an amino group, a ($C_1$–$C_6$)-alkylamino group, a di($C_1$–$C_6$)-alkylamino group, a di[hydroxy-($C_2$–$C_4$)-alkyl]amino group, a hydroxy-($C_2$–$C_4$)-alkylamino group, a trifluoromethyl group, an acetamido group, a —C(O)$CH_3$ group, a —C(O)$CF_3$ group, an —Si($CH_3$)$_3$ group, a hydroxy-($C_1$–$C_4$)-alkyl group or a dihydroxy-($C_2$–$C_4$)-alkyl group, or R5 and R6 together form an —O—$CH_2$—O— bridge; provided that the R4 and R7 groups or the R5 and R8 groups do not simultaneously denote an amino group.

Compounds of formula (I) are, for example: 4-amino-2-{[5-amino-2-(2-hydroxyethoxy)phenylamino]methyl}phenol; 4-amino-2-{[5-amino-4-(2-hydroxyethoxy)phenylamino]methyl}phenol; 2-[4-amino-2-(3,5-diaminobenzylamino)phenoxy]ethanol; 2-[4-amino-2-(4-dimethylaminobenzylamino)phenoxy]ethnophenoxy) ethanol; 2-{4-amino-2-[(pyridin-2-ylmethyl)amino]phenoxy}ethanol; 2-[4-amino-2-(2-methoxybenzylamino)phenoxy]ethanol; 2-[4-amino-2-(2-aminobenzylamino)phenoxy]ethanol; 3-[(4-{[5-amino-2-(2-hydroxyethoxy)phenylamino]methyl}phenyl)-(2-cyanoethyl)amino]propionitrile; 2-[4-amino-2-(4-aminobenzylamino)phenoxy]ethanol; 2-[(4-{[5-amino-2-(2-hydroxyethoxy)phenylamino]methy}phenyl)-(2-hydroxyethyl)amino]ethanol; 2-{[5-amino-2-(2-hydroxyethoxy)phenylamino]methyl}benzene-1,4-diol; 2-[4-amino-2-(4-nitrobenzylamino)phenoxy]ethanol; 2-[4-amino-2-(3-aminobenzylamino)phenoxy]ethanol; 2-[4-{[5-amino-2-(2-hydroxyethoxy)phenylamino]methyl}phenoxy)ethanol; N-(4-{[5-amino-2-(2-hydroxyethoxy)phenylamino]methyl}phenyl)acetamide; 4-{[5-amino-2-(2-hydroxyethoxy)phenylamino]methyl}phenol; 2-{[5-amino-2-(2-hydroxyethoxy)phenylamino]methyl}phenol; 3-{[5-amino-2-(2-hydroxyethoxy)phenylamino]methyl}phenol; 4-{[5-amino-2-(2-hydroxyethoxy)phenylamino]methyl}benzoic acid; 2-[4-amino-2-(2-morpholin-4-ylbenzylamino)phenoxy]ethanol; 3-[4-amino-2-(3,5-diaminobenzylamino)phenoxy]propanol; 3-[4-amino-2-(4dimethylaminobenzylamino)-phenoxy]propanol; 3-[4-amino-2-(4-amino-2-[4-methoxybenzylamino)phenoxy]propanol; 3-(4-amino-2-benzylaminophenoxy)propanol; 3-{4-amino-2-[(pyridin-2-ylmethyl)amino]phenoxy}propanol; 3-[4-amino-2-(2-methoxybenzylamino)phenoxy]propanol; 3-[4amino-2-(2-aminobenzylamino)phenoxy]propanol; 3-[4-amino-2-(4-aminobenzylamino)phenoxy]-propanol; 3-[(4-{[5-amino-2-(2-hydroxyethoxy)phenylamino]methyl}phenyl)-(2-hydroxyethyl)amino]propanol, 3-[4-amino-2-(4nitrobenzylamino)phenoxy]propanol; 3-[4-amino-2-(3-aminobenzylamino)phenoxy]propanol; 3-(4-{[5-amino-2-(2-hydroxyethoxy)phenylamino]methyl}phenoxy)propanol; 4-{[5-amino-2-(3-hydroxypropoxy)phenylamino]

methyl}phenol; 2-{[5-amino-2-(3-hydroxypropoxy)phenylamino]methyl}phenol; 2-{[5-amino-2-(3-hydroxypropoxy)phenylamino]methyl}phenol; 3-[4-amino-2-(2-morpholin-4-ylbenzylamino)phenoxy]propanol; $N^3$-benzyl-1,3-diamino-4-(2-methoxyethoxy)benzene; $N^3$-(3-aminobenzyl-1,3-diamino-4-(2-methoxyethoxy)benzene; $N^3$-(2-aminobenzyl)-1,3-diamino-4-(2-methoxyethoxy)benzene; $N^3$-(4-aminobenzyl)-1,3-diamino-4-(2-methoxyethoxy)benzene; 3-{[5-amino-2-(2-merhoxyethoxy)phenylamino]methyl}phenol; 2-{[5-amino-2-(2-methoxyethoxy)phenylamino]methyl}phenol; 4-{[5-amino-2-(2-methoxyethoxy)phenylamino]methyl}phenol; $N^3$-benzyl-1,3-diamino-4-methoxybenzene; $N^3$-(3-aminobenzyl)-1,3-diamino-4-methoxybenzene; $N^3$-(2-aminobenzyl)-1,3-diamino-4-methoxybenzene; $N^3$-(4-aminobenzyl)-1,3-diamino-4-methoxybenzene; 3-{[5-amino-2-methoxyphenylamino]methyl}phenol; 2-{[5-amino-2-methoxyphenylamino]methyl}phenol; 4-{[5-amino-2-methoxyphenylamino]methyl}phenol; $N^3$-benzyl-1,3-diamino-4-fluorobenzene; $N^3$-(3-aminobenzyl)-1,3-diamino-4-fluorobenzene; $N^3$-(2-aminobenzyl)-1,3-diamino-4-fluorobenzene; $N^3$-(4-aminobenzyl)-1,3-diamino-4-fluorobenzene; 3-{[5-amino-2-fluorophenylamino]methyl}phenol; 2-{[5-amino-2-fluorophenylamino]methyl}phenol, and 4-{[5-amino-2-fluoro-phenylamino]methyl}phenol, as well as the salts thereof.

Preferred compounds of formula (I) are those wherein (i) R2 and R3 denote hydrogen or (ii) R1 denotes a $C_2$–$C_4$-hydroxyalkoxy group and R2 and R3 denote hydrogen or (iii) R1 denotes a $C_2$–$C_4$-hydroxyalkoxy group, R2 and R3 denote hydrogen and four of the R4 to R8 groups denote hydrogen while the remaining R4 to R8 groups denote hydrogen, a methoxy group, a hydroxyl group, a methyl group or an amino group.

Particularly preferred are the following compounds of formula (I): 2-(4-amino-2-benzylaminophenoxy)ethanol; 2-[4-amino-2-(2-aminobenzylamino)phenoxy]ethanol; 2-[4-amino-2-(4-aminobenzylamino)phenoxy]ethanol; 2-[4-amino-2-(3-aminobenzylamino)phenoxy]ethanol; 4-{[5-amino-2-(2-hydroxyethoxy)phenylamino]-methyl}phenol; 3-{[5-amino-2-(2-hydroxyethoxy)phenylamino]methyl}phenol and 2-{[5-amino-2-(2-hydroxyethoxy)phenylamino]methyl}phenol, and the salts thereof.

The N-benzyl-m-phenylenediamine derivatives of formula (I) of the invention can be prepared by known methods of synthesis. For example, the synthesis of the compounds of the invention can be accomplished by reductive amination of a derivative of formula (II) with an amine of formula (III) followed by elimination of the protective group

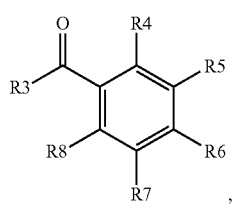

(II)

-continued

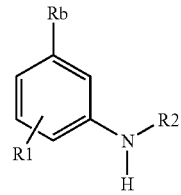

(III)

wherein Rb stands for NHRa (wherein Ra denotes a protective group described, for example, in the chapter on "Protective Groups", in Organic Synthesis, Chapter 7, Wiley Interscience 1991) or $NH_2$, and R1, R2, R3, R4, R5, R6, R7 and R8 have the same meaning as in formula (I).

The compounds of formula (I) are eminently suited as couplers in the oxidative system for dyeing keratin fibers.

Another object of the present invention are therefore agents for oxidative dyeing of keratin fibers, for example hair, furs, feathers or wool, particularly human hair, based on a developer-coupler combination containing as the coupler at least one N-benzyl-m-phenylenediamine derivative of general formula (I).

The compounds of formula (I) can be used as the free bases as well as in the form of their physiologically tolerated salts with inorganic or organic acids, for example hydrochloric acid, sulfuric acid, phosphoric acid, acetic acid, propionic acid, lactic acid or citric acid.

The N-benzyl-m-phenylenediamine derivatives of formula (I) can be present in the colorant of the invention in a total amount of about 0.005 to 20 wt. %, an amount of about 0.01 to 5 wt. % and particularly 0.1 to 2.5 wt. % being preferred.

Preferred developers are, for example 1,4-diaminobenzene (p-phenylenediamine); 1,4-diamino-2-methylbenzene (p-toluylenediamine); 1,4-diamino-2,6-dimethylbenzene; 1,4-diamino-3,5-diethylbenzene; 1,4-diamino-2,5-dimethylbenzene; 1,4-diamino-2,3-dimethylbenzene; 2-chloro-1,4-diaminobenzene; 1,4-diamino-2-(thiophen-2-yl)benzene; 1,4-diamino-2-(thiophen-3-yl)benzene; 1,4-diamino-2-(pyridin-3-yl)benzene; 2,5-diaminobiphenyl; 1,4-diamino-2-methoxymethylbenzene; 1,4-diamino-2-aminomethylbenzene; 1,4-diamino-2-hydroxymethylbenzene; 1,4-diamino-2-(2-hydroxyethoxy)-benzene; 2-[2-(acetylamino)ethoxy]-1,4-diaminobenzene; 4-phenylaminoaniline; 4-dimethylaminoaniline; 4-diethylaminoaniline; 4-dipropylaminoaniline; 4-[ethyl-(2-hydroxyethyl)amino]aniline; 4-[di(2-hydroxyethyl)amino]aniline; 4-[di(2-hydroxyethyl)amino]-2-methylaniline; 4-[(2-methoxyethyl)amino]aniline; 4-[(3-hydroxypropyl)amino]aniline; 4-[(2,3-dihydroxypropyl)amino]aniline; 1,4-diamino-2-(2-hydroxyethyl)benzene; 1,4-diamino-2-(1-hydroxyethyl)benzene; 1,4-diamino-2-(1-methylethyl)benzene; 1,3-bis-[(4-aminophenyl)(2-hydroxyethyl)amino]-2-propanol; 1,4-bis-[(4-aminophenyl)amino]butane; 1,8-bis-(2,5-diaminophenoxy)-3,6-dioxaoctane; 4-amino-phenol; 4-amino-3-methylphenol; 4-amino-3-(hydroxymethyl)phenol; 4-amino-3-fluorophenol; 4-methylaminophenol; 4-amino-2-(aminomethyl)phenol; 4-amino-2-(hydroxymethyl)phenol; 4-amino-2-fluorophenol; 4-amino-2-[(2-hydroxyethyl)amino]methylphenol; 4-amino-2-methylphenol; 4-amino-2-(methoxymethyl)phenol; 4-amino-2-(2-hydroxyethyl)phenol; 5-aminosalicylic acid; 2,5-diaminopyridine; 2,4,5,6-tetraaminopyrimidine; 2,5,6-triamino-4-(1H)-pyrimidone; 4,5-diamino-1-(2-hydroxyethyl)-1H-pyrazole; 4,5-diamino- 1-(1-methylethyl)-1H-pyrazole; 4,5-diamino-1-[(4-methylphenyl)methyl]-1H-pyrazole; 1-[(4-chlorophenyl)methyl]-4,5-diamino-1H-pyrazole; 4,5-diamino-1-methyl-1H-pyrazole; 2-aminophenol; 2-amino-6-methylphenol; 2-amino-5-methylphenol and 2,4-dihydroxyphenol.

In addition to the couplers of formula (I), the colorant of the invention can optionally also contain other known couplers, for example N-(3-dimethylaminophenyl)urea; 2,6-diaminopyridine; 2-amino-4-[(2-hydroxyethyl)amino]anisole; 2,4-diamino-1-fluoro-5-methylbenzene; 2,4-diamino-1-methoxy-5-methylbenzene; 2,4-diamino-1-ethoxy-5-methylbenzene; 2,4-diamino-1-(2-hydroxyethoxy)-5-methylbenzene; 2,4-di[(2-hydroxyethyl)amino]-1,5-dimethoxybenzene; 2,3-diamino-6-methoxypyridine; 3-amino-6-methoxy-2-(methylamino)pyridine; 2,6-diamino-3,5-dimethoxypyridine; 3,5-diamino-2,6-dimethoxypyridine; 1,3-diaminobenzene; 2,4-diamino-1-(2-hydroxyethoxy)benzene; 1,3-diamino-4-(2,3-dihydroxypropoxy)benzene; 1,3-diamino-4-(3-hydroxypropoxy)benzene; 1,3-diamino-4-(2-methoxyethoxy)benzene; 2,4-diamino-1,5-di(2-hydroxyethoxy)benzene; 1-(2-aminoethoxy)-2,4-diaminobenzene; 2-amino-1-(2-hydroxyethoxy)-4-methylaminobenzene; 2,4-diaminophenoxyacetic acid; 3-[di(2-hydroxyethyl)amino]aniline; 4-amino-2-di[(2-hydroxyethyl)amino]-1-ethoxybenzene; 5-methyl-2-(1-methylethyl)phenol; 3-[(2-hydroxyethyl)amino]aniline; 3-[(2-aminoethyl)amino]aniline; 1,3-di(2,4-diaminophenoxy)propane; di(2,4-diaminophenoxy)methane; 1,3-diamino-2,4-dimethoxybenzene; 2,6-bis(2-hydroxyethyl)aminotoluene; 4-hydroxyindole; 3-dimethylaminophenol; 3-diethylaminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methylphenol; 3-amino-2-chloro-6-methylphenol; 3-aminophenol; 2-[(3-hydroxyphenyl)amino]acetamide; 5-[(2-hydroxyethyl)amino]-4-methoxy-2-methylphenol; 5-[(2-hydroxyethyl)amino]-2-methylphenol; 3-[(2-hydroxyethyl)amino]phenol; 3-[(2-methoxyethyl)amino]phenol; 5-amino-2-ethylphenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2-methylphenol; 2-amino-3-hydroxypyridine; 2,6-dihydroxy-3,4-dimethylpyridine; 5-amino-4-chloro-2-methylphenol; 1-naphthol; 2-methyl-1-naphthol; 1,5-dihydroxynaphthalene; 1,7-dihydroxynaphthalene; 2,3-dihydroxynaphthalene; 2,7-dihydroxynaphthalene; 2-methyl-1-naphthol acetate; 1,3-dihydroxybenzene; 1-chloro-2,4-dihydroxybenzene; 2-chloro-1,3-dihydroxybenzene; 1,2-dichloro-3, 5-dihydroxy-4-methylbenzene; 1,5-dichloro-2,4-dihydroxybenzene; 1,3-dihydroxy-2-methylbenzene; 3,4-methylenedioxyphenol; 3,4-methylenedioxyaniline; 5-[(2-hydroxyethyl)amino]-1,3-benzodioxole; 6-bromo-1-hydroxy-3,4-methylenedioxybenzene; 3,4-diaminobenzoic acid; 3,4-dihydro-6-hydroxy-1,4(2H)-benzoxazine; 6-amino-3,4-dihydro-1,4[2H]-benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolinedione.

The couplers and developers can be present in the colorant of the invention either individually or in admixture with one another, the total amount of each of the couplers and developers in the colorant of the invention being about 0.005 to 20 wt. % preferably about 0.01 to 5 wt. % and particularly 0.1 to 2.5 wt. % (based on the total amount of colorant). The total amount of the developer-coupler combination contained in the colorant described herein is preferably about 0.01 to 20 wt. %, an amount of about 0.02 to 10 wt. % and especially 0.2 to 6 wt. % being particularly preferred. In general, the developers and couplers are used in approximately equimolar amounts. It is not disadvantageous, however, if the developers are present in a certain excess or deficiency [for example in a (coupler : developer) ratio of 1:2 to 1:0.5].

Moreover, the colorant of the invention can also contain other dye components, for example 6-amino-2-methylphenol and 2-amino-5-methylphenol, as well as common direct dyes, for example triphenylmethane dyes such as 4-[(4'-aminophenyl)-(4'-imino-2",5"-cyclohexadien-1"-ylidene)methyl]-2-methylaminobenzene monohydrochloride (Color Index [C.I.] 42 510) and 4-[(4'-amino-3'-methylphenyl)-(4"-imino-3"-methyl-2",5"-cyclohexadien-1"-ylidene)methyl)-2-methylaminobenzene monohydrochloride (C.I. 42 520), aromatic nitro dyes such as 4-(2'-hydroxyethyl)aminonitrotoluene; 2-amino-4,6-dinitrophenol; 2-amino-5-(2'-hydroxyethyl)aminonitrobenzene; 2-chloro-6-(ethylamino)-4-nitrophenol; 4-chloro-N-(2-hydroxyethyl)-2-nitroaniline; 5-chloro-2-hydroxy-4-nitroaniline; 2-amino-4-chloro-6-nitrophenol and 1-(2'-ureidoethyl)amino-4-nitrobenzene, azo dyes such as sodium 6-[(4'-aminophenyl)azo]-5-hydroxynaphthalene-1-sulfonate (C.I. 14 805) and disperse dyes, for example 1,4-diaminoanthraquinone and 1,4,5,8-tetraaminoanthraquinone. The colorants of the invention can contain the aforesaid dye components in an amount from about 0.1 to 4 wt. %.

The couplers and developers as well as the other dye components, provided they are bases, can, of course, also be used in the form of their physiologically tolerated salts with organic or inorganic acids, for example hydrochloric acid or sulfuric acid, or—if they contain aromatic OH groups—in the form of their salts with bases, for example as alkali metal phenoxides.

Moreover, if the colorants of the invention are to be used for coloring hair, they can also contain other common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be in the form of, for example, a solution, particularly an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The said constituents are used in amounts commonly employed for such purposes, for example the wetting agents and emulsifiers at a concentration of about 0.5 to 30 wt. %, the thickeners in an amount from about 0.1 to 25 wt. % and the hair-care agents at a concentration from about 0.1 to 5 wt. %.

Depending on the composition, the colorant of the invention can be weakly acidic, neutral or alkaline. In particular, it has a pH of 6.5 to 11.5. Adjustment to a basic pH is preferably done with ammonia, but it can also be done with an organic amine, for example monoethanolamine and triethanolamine, or with an inorganic base such as sodium hydroxide and potassium hydroxide. Suitable for adjustment to an acidic pH are inorganic or organic acids, for example phosphoric acid, acetic acid, citric acid or tartaric acid.

For oxidative dyeing of hair, the afore-described colorant is mixed with an oxidant just before use, and the resulting mixture is applied to hair in an amount sufficient for the hair-dyeing treatment, in general about 50 to 200 grams, depending on the hair fullness. The ready-to-use oxidative hair colorant obtained after mixing with the oxidant preferably has a pH of 6.5 to 11.5.

Suitable oxidants for developing the hair coloration are mainly hydrogen peroxide or its products of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from about 5:1 to 1:2, but preferably about 1:1. Larger amounts of oxidant are used primarily at higher dye concentrations in the hair colorant or when stronger bleaching of the hair is wanted at the same time. The mixture is allowed to act on the hair at 15 to 50° C. for about 10 to 45 min, preferably 30 min, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing an N-benzyl-m-phenylenediamine derivative of formula (I) as coupler give hair colorations of excellent color stability, particularly in terms of light fastness, wash fastness and rubbing fastness. As far as the dyeing properties are concerned, the hair colorants of the invention provide a wide range of different shades from blond to brown, purple, violet and even blue and black, depending on the the kind and composition of the dye components. The shades are noteworthy for their high color intensity. The very good coloring properties of the hair colorant of the present patent application also manifest themselves in that this colorant makes it possible to dye gray hair, previously not damaged chemically, without any problems and with good covering power.

The N-benzyl-m-phenylenediamine derivatives of formula (I) are highly water-soluble and give colorations of high color intensity and excellent color stability, particularly in terms of light fastness, wash fastness and rubbing fastness. Moreover, they have excellent storage stability, particularly as constituents of the oxidation colorants described herein.

The following examples illustrate the object of the invention in greater detail without limiting its scope.

EXAMPLES

Example 1

A. Synthesis of tert.butyl[3-amino-4-(2-hydroxyethoxy)phenyl]carbamate

To a solution of 10.7 g (100 mmol) of 2-(2,4-diaminophenoxy)ethanol in 300 mL of acetonitrile was added dropwise a solution of 16.8 g of $NaHCO_3$ in 100 mL of water, followed by the addition of 22 g (100 mmol) of ditert.butyl dicarbonate. The reaction mixture was allowed to agitate for 6 hours. At the end of the reaction, the reaction mixture was poured into 100 mL of dichloromethane, and the organic phase was extracted with dilute hydrochloric acid. The aqueous phase was then made alkaline with saturated 2N sodium hydroxide solution [sic–Translator] and then extracted with dichloromethane. The organic phase was dried over sodium sulfate and then distilled off in a rotary evaporator.

This gave 10.3 g (38% of the theoretical) of tert.butyl[3-amino-4-(2-hydroxyethoxy)-phenyl]carbamate.

$^1$H-NMR (300 MHz, $CDCl_3$): δ=7.26 (br s, 1H); 6.95 (d, 1H); 6.72 (d, 1H); 6.34 (s, 1H); 4.77 (m, 2H); 3.9 (m, 2H); 1.50 (s, 9H).

B. Synthesis of the 1,3-diaminobenzene derivatives.

0.031 g (0.15 mmol) of the tert.butyl (3-aminophenyl)carbamate from Example 1A and 0.1 mmol of the appropriate aldehyde were dissolved in methanol (dried over molecular sieve). Following the addition of 10 mg of molecular sieve, the reaction mixture was allowed to agitate for 7 hours. Then, 0.3 mL of a solution of borane-tetrahydrofuran complex (1 M in tetrahydrofuran) was added at 0° C., and the reaction mixture was allowed to agitate one hour at room temperature. At the end of the reaction, the reaction mixture was poured into water and extracted with ethyl acetate. The organic phase was dried with magnesium sulfate. The solvent was distilled off in a rotary evaporator, and the residue was purified on silica gel with petroleum ether/ethyl acetate (1:1). The resulting product in 4 mL of ethanol and 1.5 mL of a 2.9-molar ethanolic hydrochloric acid solution was heated to 50° C. The precipitate was filtered off, washed twice with 1-mL portions of ethanol and then dried.

a. 2-(4-Amino-2-benzylaminophenoxy)ethanol hydrochloride

Aldehyde used: benzaldehyde

Mass spectrum: $MH^+$ 259 (100)

b. 2-[4-Amino-2-(4-aminobenzylamino)phenoxy]ethanol hydrochloride

Aldehyde used: tert.butyl (4-formylphenyl)carbamate

Mass spectrum: $MH^+$ 274 (25)

c. 2-[4-Amino-2-(3-aminobenzylamino)phenoxy]ethanol hydrochloride

Aldehyde used: 3-aminobenzaldehyde

Mass spectrum: $MH^+$ 274 (80)

d. 2-[4-Amino-2-(2-aminobenzylamino)phenoxy]ethanol hydrochloride

Aldehyde used: 2-aminobenzaldehyde

Mass spectrum: $MH^+$ 274 (10)

e. 4-Amino-2-{[5-amino-2(4)-(2-hydroxyethoxy)phenylamino]methyl}phenol hydrochloride Aldehyde used: tert.butyl (3-formyl-4-hydroxyphenyl)carbamate Mass spectrum: $MH^+$ 293 (100)

f. 2-[4-Amino-2-(3,5-diaminobenzylamino)phenoxy]ethanol hydrochloride

Aldehyde used: 3,5 diaminobenzaldehyde

Mass spectrum: $MH^+$ 289 (100)

g. 2-[4-Amino-2-(4-dimethylaminobenzylamino)phenoxy]ethanol

Aldehyde used: 4-dimethylaminobenzaldehyde
Mass spectrum: MH$^+$ 302 (10)

h. 2-[4-Amino-2-(4-methoxvbenzylamino)phenoxy]ethanol hydrochloride
Aldehyde used: 4-methoxybenzaldehyde
Mass spectrum: MH$^+$ 229 (100)

i. 2-[4-Amino-2-(2-methoxybenzylamino)phenoxy]ethanol hydrochloride
Aldehyde used: 2-methoxybenzaldehyde
Mass spectrum: MH$^+$ 229 (100)

j. 3-[(4-{[5-Amino-2-(2-hydroxyethoxy)phenylamino]methyl}phenyl)-(2-cyanoethyl)amino]propionitrile hydrochloride
Aldehyde used: 3-[(2-cyanoethyl)-(4-formylphenyl)amino]propionitrile
Mass spectrum: MH$^+$ 380 (100)

k. 2-[(4-{[5-Amino-2-(2-hydroxyethoxy)phenylamino]methyl}phenyl)-(2-hydroxyethyl)amino]ethanol hydrochloride
Aldehyde used: 4-[bis-(2-hydroxyethyl)amino]benzaldehyde
Mass spectrum: MH$^+$ 362 (10)

l. 1,4-Dihydroxy-2-{[5-amino-2-(2-hydroxyethoxy)phenylamino]methyl}benzene hydrochloride
Aldehyde used: 2,5-dihydroxybenzaldehyde
Mass spectrum: MH$^+$ 291 (50)

m. 2-[4-Amino-2-(4-nitrobenzylamino)phenoxy]ethanol hydrochloride
Aldehyde used: 4-nitrobenzaldehyde
Mass spectrum: MH$^+$ 304 (20)

n. 2-(4-{[5-Amino-2-(2-hydroxyethoxy)phenylamino]methyl}phenoxy)ethanol hydrochloride
Aldehyde used: 4-(2-hydroxyethoxy)benzaldehyde
Mass spectrum: MH$^+$ 319 (100)

o. N-(4-{[5-Amino-2-(2-hydroxyethoxy)phenylamino]methyl}phenyl)acetamide hydrochloride
Aldehyde used: 4-acetamidobenzaldehyde
Mass spectrum: MH$^+$ 316 (100)

p. 4-{[5-Amino-2-(2-hydroxyethoxy)phenylamino]methyl}phenol hydrochloride
Aldehyde used: 4-hydroxybenzaldehyde
Mass spectrum: MH$^+$ 275 (80)

q. 3-{[5-Amino-2-(2-hydroxyethoxy)phenylamino]methyl}phenol hydrochloride
Aldehyde used: 3-hydroxybenzaldehyde
Mass spectrum: MH$^+$ 203 (100)

r. 2-{[5-Amino-2-(2-hydroxyethoxy)phenylamino]methyl}phenol hydrochloride
Aldehyde used: 2-hydroxybenzaldehyde
Mass spectrum: MH$^+$ 275 (40)

s. 2-{[5-Amino-2-(2-hydroxyethoxy)phenylamino]methyl}benzoic acid hydrochloride
Aldehyde used: 4-formylbenzoic acid
Mass spectrum: MH$^+$ 303 (45)

t. 2-[4-Amino-2-(2-morpholin-4-ylbenzylamino)phenoxy]ethanol hydrochloride
Aldehyde used: 2-(morpholin-4-yl)benzaldehyde
[Mass spectrum missing·Translator]

u. Synthesis of 2-[2-amino-4-(benzylamino)phenoxy]ethanol 2.66 g (10 mmol) of 2-(2,4-diaminophenoxy)ethanol and 1.06 g (10 mmol) of benzaldehyde were dissolved in methanol (dried over molecular sieve). After addition of 10 mg of molecular sieve, the reaction mixture was allowed to agitate 7 hours. Then, 20 mL of a solution of borane-tetrahydrofuran com-plex (1 M in tetrahydrofuran) was added at 0° C., and the reaction mixture was allowed to agitate one hour at room temperature. At the end of the reaction, the reaction mixture was filtered and hydrolyzed. The precipitate was filtered off, washed with water and then dried.

$^1$H-NMR (300 MHz, D$_6$MSO): δ=7.21 (m, 5H); 6.56 (d, 1H); 6.0 (s, 1H); 5.83 (d, 1H); 4.77 (s, 2H); 3.7 (t, 2H); 3.63 (t, 2H).

Examples 2 to 23

Hair Colorants

Hair colorant solutions having the following composition were prepared:

| | | |
|---|---|---|
| 1.25 | mmol | of coupler of formula (I) as per Table 1 |
| 1.25 | mmol | of developer as per Table 1 |
| 1.0 | g | of potassium oleate (8% aqueous solution) |
| 1.0 | g | of ammonia (22% aqueous solution) |
| 1.0 | g | of ethanol |
| 0.3 | g | of ascorbic acid |
| to 100.0 | g | water |

Just before use, 50 g of the foregoing coloring solution was mixed with 50 g of a 6% aqueous hydrogen peroxide solution. The mixture was then applied to bleached hair. After an exposure time of 30 min at 40° C., the hair was rinsed with water, washed with a commercial shampoo and dried. The resulting color shades are presented in Table 1.

TABLE 1

| | | Developer | | | |
|---|---|---|---|---|---|
| Example No. | Coupler of formula (I) | I. 1,4-Di-amino-benzene | II. 2,5-Diamino-toluene sulfate | III. 2,5-Diamino-phenyl-ethanol sulfate | IV. 4,5-Diamino-1-(2'-hydroxy-ethyl)pyrazole sulfate |
| 2 | As per Ex. 1a | dark blue | dark blue | dark blue | purple shades |
| 4 | As per Ex. 1b | dark blue | dark blue | dark blue | purple shades |
| 5 | As per Ex. 1c | dark blue | dark blue | dark blue | purple shades |
| 6 | As per Ex. 1d | dark blue | dark blue | dark blue | purple shades |
| 7 | As per Ex. 1e | dark blue | blue | blue | purple shades |

TABLE 1-continued

| Example No. | Coupler of formula (I) | Developer I. 1,4-Di-amino-benzene | II. 2,5-Diamino-toluene sulfate | III. 2,5-Diamino-phenyl-ethanol sulfate | IV. 4,5-Diamino-1-(2'-hydroxy-ethyl)pyrazole sulfate |
|---|---|---|---|---|---|
| 8 | As per Ex. 1f | dark blue | dark blue | dark blue | purple shades |
| 9 | As per Ex. 1g | dark blue | blue | blue | purple shades |
| 10 | As per Ex. 1h | dark blue | blue | blue | purple shades |
| 11 | As per Ex. 1i | dark blue | blue | blue | purple shades |
| 12 | As per Ex. 1j | blue | sl. blue | sl. blue | purple shades |
| 13 | As per Ex. 1k | blue | blue | blue | purple shades |
| 14 | As per Ex. 1l | blue | sl. blue | sl. blue | purple shades |
| 15 | As per Ex. 1m | blue | blue | blue | purple shades |
| 16 | As per Ex. 1n | blue | blue | blue | purple shades |
| 17 | As per Ex. 1o | blue | blue | blue | purple shades |
| 18 | As per Ex. 1p | blue | blue | blue | purple shades |
| 19 | As per Ex. 1q | blue | blue | blue | purple shades |
| 20 | As per Ex. 1r | blue | blue | blue | purple shades |
| 21 | As per Ex. 1s | blue | sl. blue | sl. blue | purple shades |
| 22 | As per Ex. 1t | blue | sl. blue | sl. blue | purple shades |
| 23 | As per Ex. 1u | blue | blue | blue | purple shades |

Examples 24 to 35

Hair Colorants

Hair colorant solutions of the following composition were prepared:

```
X g   of 1,3-diaminobenzene [coupler K1 to K3 of formula (I) as
      per Table 4]
U g   of developer E8 to E15 as per Table 2
Y g   of coupler K12 to K36 as per Table 4
Z g   of direct dye D2 as per Table 3
10.0 g of potassium oleate (8% aqueous solution)
10.0 g of ammonia (22% aqueous solution)
10.0 g of ethanol
 0.3 g of ascorbic acid
to 100.0 g water
```

Just before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. Table 5 shows the coloring results.

Examples 36 to 47

Hair Colorants

Dye carriers in cream form and having the following composition were prepared:

```
X g   of 1,3-diaminobenzene (coupler K1 to K3 of formula (I) as
      per Table 4)
U g   of developer E8 to E15 as per Table 2
Y g   of coupler K12 to K36 as per Table 4
Z g   of direct dye D2 as per Table 3
15.0 g of cetyl alcohol
 0.3 g of ascorbic acid
 3.5 g of sodium lauryl alcohol diethylene glycol ether sulfate,
      28% aqueous solution
 3.0 g of ammonia, 22% aqueous solution
 0.3 g of sodium sulfite, anhydrous
to 100.0 g water
```

Just before use, 30 g of the foregoing coloring cream was mixed with 30 g of a 6% solution of hydrogen peroxide. The mixture was then applied to the hair. After an exposure time of 30 min at 40° C., the hair was rinsed with water, washed with a commercial shampoo and dried. The coloring results are presented in Table 6.

TABLE 2

| | Developers |
|---|---|
| E8 | 1,4-diaminobenzene |
| E9 | 1,4-diamino-2-(2-hydroxyethyl)benzene sulfate |
| E12 | 4-aminophenol |
| E13 | N,N-bis(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

| | Direct Dye |
|---|---|
| D2 | 6-chloro-2-ethylamino-4-nitrophenol |

TABLE 4

| | Couplers |
|---|---|
| K1 | 2-(4-amino-2-benzylaminophenoxy)ethanol hydrochloride |
| K2 | 2-[4-amino-2-(4-aminobenzylamino)phenoxy]ethanol hydrochloride |
| K3 | 4-amino-2-{[5-amino-2 or 4-(2-hydroxyethoxy)phenylamino]-methyl}-phenol hydrochloride |
| K12 | 2-amino-4-(2'-hydroxyethyl)aminoanisole sulfate |
| K13 | 1,3-diamino-4-(2-hydroxyethoxy)benzene sulfate |
| K21 | 3-aminophenol |
| K22 | 5-amino-2-methylphenol |

TABLE 4-continued

| | Couplers |
|---|---|
| K23 | 3-amino-2-chloro-6-methylphenol |
| K31 | 1,3-dihydroxybenzene |
| K32 | 2-methyl-1,3-dihydroxybenzene |
| K33 | 1-chloro-2,4-dihydroxybenzene |
| K36 | 2-amino-5-methylphenol |

TABLE 5

Hair Colorants

| | Example No. | | | | | |
|---|---|---|---|---|---|---|
| | 24 | 25 | 26 | 27 | 28 | 29 |
| Dyes | (Quantity of dye in grams) | | | | | |
| K1 | 0.15 | 0.16 | 0.09 | 0.12 | 0.15 | 0.18 |
| E8 | 0.30 | | | | | |
| E9 | | | | | 0.25 | 0.30 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K31 | 0.20 | | | 0.15 | 0.20 | 0.10 |
| K32 | | 0.20 | | 0.10 | | 0.10 |
| K33 | | | 0.20 | | | |
| K36 | 0.03 | | | 0.05 | | |
| Dyeing result | blond | blond | blond | blond | blond | blond |

| | Example No. | | | | | |
|---|---|---|---|---|---|---|
| | 30 | 31 | 32 | 33 | 34 | 35 |
| Dyes | (Quantity of dye in grams) | | | | | |
| K2 | 0.15 | | 0.09 | | 0.15 | 0.12 |
| K3 | | 0.16 | | 0.12 | | 0.16 |
| E8 | 0.30 | | | | | |
| E9 | | | | | 0.25 | 0.30 |
| E15 | | 0.25 | 0.30 | 0.25 | | |
| K12 | | | 0.05 | | | |
| K13 | | | | 0.05 | | |
| K21 | 0.05 | | | | | |
| K22 | | 0.05 | | | | |
| K23 | | | 0.05 | 0.10 | 0.10 | 0.10 |
| K31 | 0.20 | | | 0.15 | 0.20 | 0.10 |
| K32 | | 0.20 | | 0.10 | | 0.10 |
| K33 | | | 0.20 | | | |
| Dyeing result | blond | blond | blond | blond | blond | blond |

TABLE 6

Hair Colorants

| | Example No. | | | | | |
|---|---|---|---|---|---|---|
| | 36 | 37 | 38 | 39 | 40 | 41 |
| Dyes | (Quantity of dye in grams) | | | | | |
| K1 | 0.70 | 1.50 | 1.25 | 0.18 | 0.18 | 0.18 |
| E8 | 1.50 | | | | | |
| E13 | | 1.60 | | | | 0.70 |
| E15 | | | 1.80 | 0.70 | 0.70 | |
| K12 | 0.60 | | | | | |
| K23 | | | 0.05 | 0.10 | 0.10 | 0.10 |
| K31 | 1.10 | 1.10 | 1.10 | 0.40 | 0.40 | 0.40 |
| D2 | | | | 0.10 | 0.10 | 0.10 |
| Dyeing result | black | black | black | brown | brown | brown |

TABLE 6-continued

Hair Colorants

| | Example No. | | | | | |
|---|---|---|---|---|---|---|
| | 42 | 43 | 44 | 45 | 46 | 47 |
| Dyes | (Quantity of dye in grams) | | | | | |
| K2 | 0.7 | | 1.15 | | 0.15 | |
| K3 | | 1.5 | | 0.18 | | 0.18 |
| E8 | 1.5 | | | | | |
| E13 | | 1.6 | | | | 0.7 |
| E15 | | | 1.8 | 0.7 | 0.7 | |
| K12 | 0.6 | | | | | |
| K23 | | | 0.05 | 0.10 | 0.10 | 0.10 |
| K31 | 1.10 | 1.10 | 1.10 | 0.40 | 0.40 | 0.40 |
| D2 | | | | 1.10 | 1.10 | 1.10 |
| Dyeing result | black | black | black | brown | brown | brown |

Unless otherwise indicated, all percentages given in the present patent application are by weight.

The invention claimed is:
1. An N-Benzyl-m-phenylenediamine derivatives of general formula (I) or the physiologically-tolerated, water-soluble salts thereof,

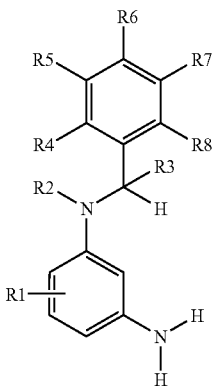

wherein R1 denotes a halogen atom, a $C_1-C_4$-alkoxy group, a $C_1-C_4$-fluoroalkoxy group, a $(C_1-C_4$-alkyl)sulfamido-$(C_2-C_4$-alkoxy) group, a $(C_1-C_4$-alkyl)sulfonyl-$(C_2-C_4$-alkoxy) group, a $C_2-C_4$-hydroxyalkoxy group, a $C_3-C_4$-dihydroxyalkoxy group, a $C_1-C_6$-alkyl group, a $C_1-C_4$-alkylthioether group, a $C_2-C_4$-aminocarbonylalkoxy group, an aminoalkyl group, a trifluoromethyl group, an —Si$(CH_3)_3$ group, a $C_1-C_4$-hydroxyalkyl group or a $C_3-C_4$-dihydroxyalkyl group;

R2 and R3 independently of each other denote hydrogen or a $C_1-C_4$-alkyl group, R4, R5, R6, R7 and R8 independently of each other denote hydrogen, a halogen atom, a hydroxyl group, a $(C_1-C_4)$-alkoxy group, a hydroxy-$(C_2-C_4)$-alkoxy group, a $(C_1-C_6)$-alkyl group, a $(C_1-C_4)$-alkylthioether group, a mercapto group, an amino group, a $(C_1-C_6)$-alkylamino group, a di$(C_1-C_6)$-alkylamino group, a di[hydroxy-$(C_2-C_4)$-alkyl]amino group, a hydroxy-$(C_2-C_4)$-alkylamino group, a trifluoromethyl group, an acetamido group, a —C(O)CH$_3$ group, a —C(O)Cf$_3$ group, an —Si(CH$_3$)$_3$ group, a hydroxy-$(C_1-C_4)$-alkyl group or a dihydroxy-$(C_2-C_4)$-alkyl group, or R5 and R6 together form an —O—CH$_2$—O— bridge;

with the proviso that R4 and R7 do not simultaneously each denote an amino group or that R5 and R8 do not simultaneously each denote an amino group; that R1 does not denote a $CH_3$ group when each of R2, R3, R4, R5, R8, R7 and R8 denotes hydrogen; that R1 does not denote a $OCH_3$ group when simultaneously R2 denotes an isopropyl group and each of R3, R4, R5, R6, R7 and R8 denote hydrogen; that R1 does not denote hydrogen when simultaneously R2 denotes an isopropyl group, R4 denotes bromine and each of R3, R5, R6, R7 and R8 denote hydrogen or R8 denotes bromine and each of R3, R4, R5, R6 and R7 denote hydrogen; and that R1 does not denote methyl when simultaneously R2 denotes an isopropyl group, R4 denotes bromine and each of R3, R5, R6, R7 and R8 denote hydrogen or RB denotes bromine and each of R3, R4, R5, R6 and R7 denote hydrogen.

2. An N-benzyl-m-phenylenediamine derivative, or a water-soluble salt thereof, wherein said N-benzyl-m-phenylenediamine derivative is selected from the group consisting of 4-amino-2-{[5-amino-2-(2-hydroxyethoxy)-phenylamino]methyl}-phenol, 4-amino-2-{[5-amino-4-(2-hydroxyethoxy)-phenylamino]methyl}-phenol, 2-[4-amino-2-(3,5-diamino-benzylamino)phenoxy]ethanol, 2-[4-amino-2-(4-dimethylamino-benzylamino)-phenoxy]-ethanol, 2-[4-amino-2-(4-methoxy-benzylamino)-phenoxy]-ethanol, 2-(4-amino-2-benzyl-aminophenoxy)-ethanol, 2-{4-amino-2-[(pyridin-2-ylmethyl)-amino]-phenoxy}-ethanol, 2-[4-amino-2-(2-methoxy-benzylamino)-phenoxy]-ethanol, 2-[4-amino-2-(2-amino-benzyl-amino)phenoxy]-ethanol, 3-[(4-{[5-amino-2-(2-hydroxy-ethoxy)-phenylamino]-methyl}-phenyl)-(2-cyanoethyl)-amino]-propionitrile, 2-[4-amino-2-(4-amino-benzylamino)-phenoxy]ethanol, 2-[(4-{[5-amino-2-(2-hydroxyethoxy)phenyl-amino]methyl}-phenyl)-(2-hydroxyethyl)amino]-ethanol, 2-{[5-amino-2-(2-hydroxyethoxy)-phenylamino]-methyl}-benzene-1,4-diol, 2-[4-amino-2-(4-nitrobenzylamino)-phenoxy]-ethanol, 2-[4-amino-2-(3-aminobenzylamino)-phenoxy]-ethanol, 2-(4-{[5-amino-2-(2-hydroxy-ethoxy)phenyl-amino]-methyl}-phenoxy)-ethanol, N-(4-{[5-amino-2-(2-hydroxy-ethoxy)-phenylamino]-methyl}-phenyl)-acetamide, 4-{[5-amino-2-(2-hydroxyethoxy)-phenylamino]methyl}-phenol, 3-{(5-amino-2-(2-hydroxyethoxy)-phenylamino]-methyl}-phenol, 2-{[5-amino-2-(2-hydroxy-ethoxy)-phenylamino]-methyl}-phenol, 4-{[5-amino-2-(2-hydroxyethoxy)-phenyl-amino]-methyl}-benzoic acid, 2-[4-amino-2-(2-morpholin-4-yl-benzylamino)-phenoxyethenol, 3-[4-amino-2-(3,5-diamino-benzylamino)phenoxy]-propanol, 3-[4-amino-2-(4-dimethylaminobenzylamino)-phenoxy]-propanol, 3-(4-amino-2-(4-methoxybenzylamino)-phenoxy]-propanol, 3-(4-amino-2-benzlamino-phenoxy)-propanol, 3-{4-amino-2-[(pyridin-2-ylmethyl)-amino]phenoxy}-propanol, 3-[4-amino-2-(2-methoxybenzylamino)phenoxy]-propanol, 3-[4-amino-2-(2-aminobenzylamino)phenoxy]-propanol, 3-[4-amino-2-(4-aminobenzyl-amino)-phenoxy]-propanol, 3-[(4-{[5-amino-2-(2-hydroxyethoxy)-phenylamino]-methyl}-phenyl)-(2-hydroxyethyl)amino]propanol, 3-[4-amino-2-(4-nitrobenzyl-amino)-phenoxy]-propanol, 3-[4-amino-2-(3-aminobenzylamino)-phenoxy]-propanol, 3-(4-{[5-amino-2-(2-hydroxyethoxy)phenylamino]-methyl}-phenoxy)-propanol, 4-{[5-amino-2-(3-hydroxypropoxy)phenylamino]-methyl}-phenol, 2-{[5-amino-2-(3-hydroxypropoxy)phenylamino]-methyl}-phenol, 2-{[5-amino-2-(3-hydroxypropoxy)-phenylamino]-methyl}-phenol, 3-[4-amino-2-(2-morpholin-4-yl-benzylamino)-phenoxy]-propanol, $N^3$-benzyl-1,3-diamino-4-(2-methoxy-ethoxy)-benzene, $N^3$-(3-aminobenzyl)-1,3-diamino-4-(2-methoxy-ethoxy)-benzene, $N^3$-(2-amino-benzyl)-1,3-diamino-4-(2-methoxyethoxy)-benzene, $N^3$-(4-aminobenzyl)-1,3-diamino-4-(2-methoxyethoxy)-benzene, 3-{[5-amino-2-(2-methoxyethoxy)-phenylamino]methyl}-phenol, 2-{[5-amino-2-(2-methoxy-ethoxy)-phenylamino]-methyl}phenol, 4-{[5-amino-2-(2-methoxy-ethoxy)-phenyl-amino]-methyl}-phenol, $N^3$-benzyl-1,3-diamino-4-methoxy-benzene, $N^3$-(3-amino-benzyl)-1,3-diamino-4-methoxybenzene, $N^3$-(2-aminobenzyl)-1,3-diamino-4-methoxybenzene, $N^3$-(4-aminobenzyl)-1,3-diamino-4-methoxybenzene, 3-{[5-amino-2-methoxy-phenylamino]-methyl}-phenol, 2-{[5-amino-2-methoxy-phenylamino]-methyl}-phenol, 4-{[5-amino-2-methoxy-phenyl-amino]-methyl}-phenol, $N^3$-benzyl-1,3-diamino-4-fluorobenzene, $N^3$-(3-aminobenzyl)-1,3-diamino-4-fluorobenzene, $N^3$-(2-aminobenzyl)-1,3-diamino-4-fluorobenzene, $N^3$-(4-aminobenzyl)-1,3-diamino-4-fluorobenzene, 3-{[5-amino-2-fluoraphenylamino]-methyl}-phenol, 2-{[5-amino-2-fluorophenyl-amino]-methyl}-phenol, and 4-{[5-amino-2-fluoro-phenylamino]methyl}-phenol.

3. The N-benzyl-m-phenylenediamine derivative, or the water-soluble salt thereof, as defined in claim 1, wherein R2 and R3 each denote hydrogen; R1 denotes a $C_2$–$C_4$-hydroxyalkoxy group and R2 and R3 each denote hydrogen; or R1 denotes a $C_2$–$C_4$-hydroxyalkyl group, R2 and R3 each denote hydrogen and four of R4, R5, R6, R7 and R8 denote hydrogen while a remaining one of R4, R5, R6, R7 and R8 denotes hydrogen, a methoxy group, a hydroxy group, a methyl group or an amino group.

4. The N-benzyl-m-phenylenediamine derivative, or the water-soluble salt thereof, as defined in claim 1, wherein said N-benzyl-m-phenylenediamine derivative is selected from the group consisting of 2-(4-amino-2-benzylamino-phenoxy)ethanol, 2-[4-amino-2-(2-aminobenzylamino)phenoxy]-ethanol, 2-[4-amino-2-(4-aminobenzylamino)phenoxy]ethanol, 2-[4-amino-2-(3-amino-benzylamino) phenoxy]ethanol, 4-{[5-amino-2-(2-hydroxyethoxy)-phenylamino]-methyl}phenol, 3-{[5-amino-2-(2-hydroxyethoxy)-phenylamino]-methyl}phenol, and 2-{[5-amino-2-(2-hydroxyethoxy)phenylamino]-methyl}phenol.

5. A composition for oxidative dyeing of keratin fibers, said composition containing at least one coupler and at least one developer;

wherein said at least one coupler comprises at least one N-benzyl-m-phenylenediamine derivative of formula (I), or a physiologically tolerated, water-soluble salt thereof, (I)

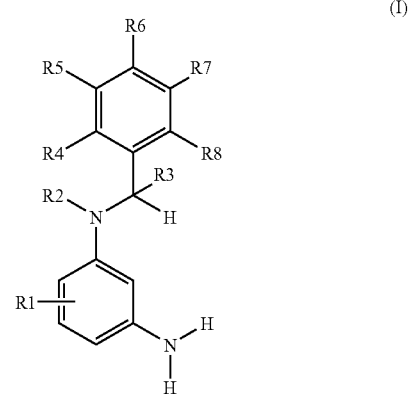

wherein R1 denotes a halogen atom, a $C_1$–$C_4$-alkoxy group, a $C_1$–$C_4$-fluoroalkoxy group, a ($C_1$–$C_4$-alkyl)sulfamido-($C_2$–$C_4$-alkoxy) group, a ($C_1$–$C_4$-alkyl)sulfonyl-($C_2$–$C_4$-alkoxy) group, a $C_2$–$C_4$-hydroxyalkoxy group, a $C_3$–$C_4$-dihydroxyalkoxy group, a $C_1$–$C_6$-alkyl group, a $C_1$–$C_4$-alkylthioether group, a $C_2$–$C_4$-aminocarbonylalkoxy group, an aminoalkyl group, a trifluoromethyl group, an —Si($CH_3)_3$ group, a $C_1$–$C_4$-hydroxyalkyl group or a $C_3$–$C_4$-dihydroxyalkyl group;

R2 and R3 independently of each other denote hydrogen or a $C_1$–$C_4$-alkyl group, R4, R5, R6, R7 and R8 independently of each other denote hydrogen, a halogen atom, a hydroxyl group, a ($C_1$–$C_4$)-alkoxy group, a hydroxy-($C_2$–$C_4$)-alkoxy group, a ($C_1$–$C_6$)-alkyl group, a ($C_1$–$C_4$)-alkylthioether group, a mercapto group, an amino group, a ($C_1$–$C_6$)-alkylamino group, a di($C_1$–$C_6$)-alkylamino group, a di[hydroxy-($C_2$–$C_4$)-alkyl]amino group, a hydroxy-($C_2$–$C_4$)-alkylamino group, a trifluoromethyl group, an acetamido group, a —C(O)$CH_3$ group, a —C(O)$CF_3$ group, an —Si($CH_3)_3$ group, a hydroxy-($C_1$–$C_4$)-alkyl group or a dihydroxy-($C_2$–$C_4$)-alkyl group, or R5 and R6 together form an —O—$CH_2$—O— bridge;

with the proviso that R4 and R7 do not simultaneously each denote an amino group or that R5 and R8 do not simultaneously each denote an amino group; that R1 does not denote a $CH_3$ group when each of R2, R3, R4, R5, R8, R7 and R8 denotes hydrogen; that R1 does not denote a $OCH_3$ group when simultaneously R2 denotes an isopropyl group and each of R3, R4, R5, R6, R7 and R8 denote hydrogen; that R1 does not denote hydrogen when simultaneously R2 denotes an isopropyl group, R4 denotes bromine and each of R3, R5, R6, R7 and R8 denote hydrogen or R8 denotes bromine and each of R3, R4, R5, R6 and R7 denote hydrogen.

6. The composition as defined in claim 5, containing from 0.005 to 20 percent by weight of said at least one N-benzyl-m-phenylenediamine derivative of formula (I), or said physiologically tolerated, water-soluble salt thereof.

7. The composition as defined in claim 5, wherein said at least one developer is selected from the group consisting of 1,4-diaminobenzene; 1,4-diamino-2-methylbenzene; 1,4-diamino-2,6-dimethylbenzene; 1,4-diamino-3,5-diethyl-benzene; 1,4-diamino-2,5-dimethylbenzene; 1,4-diamino-2,3-dimethylbenzene; 2-chloro-1,4-diaminobenzene; 1,4-diamino-2-(thiophen-2-yl)benzene; 1,4-diamino-2-(thiophen-3-yl)benzene; 1,4-diamino-2-(pyridin-3-yl)benzene; 2,5-diaminobiphenyl; 1,4-diamino-2-methoxymethylbenzene; 1,4-diamino-2-aminomethyl-benzene; 1,4-diamino-2-hydroxymethylbenzene; 1,4-diamino-2-(2-hydroxyethoxy)benzene; 2-[2-(acetylamino)ethoxy]-1,4-diaminobenzene; 4-phenylaminoaniline; 4-dimethylaminoaniline; 4-diethylaminoaniline; 4-dipropylaminoaniline; 4-[ethyl-(2-hydroxyethyl)amino]aniline; 4-[di(2-hydroxyethyl)amino]-aniline; 4-[di(2-hydroxy-ethyl)amino]-2-methylaniline; 4-[(2-methoxyethyl)amino]-aniline; 4-[(3-hydroxy-propyl)amino]aniline; 4-[(2,3-dihydroxypropyl)amino]-aniline; 1,4-diamino-2-(2-hydroxyethyl)benzene; 1,4-diamino-2-(1-hydroxyethyl)-benzene; 1,4-diamino-2-(1-methylethyl)benzene; 1,3-bis[(4-aminophenyl)-(2-hydroxyethyl)amino]-2-propanol; 1,4-bis[(4-aminophenyl)-amino]butane; 1,8-bis(2,5-diaminophenoxy)-3,6-dioxaoctane; 4-aminophenol; 4-amino-3-methylphenol; 4-amino-3-(hydroxymethyl)phenol; 4-amino-3-fluorophenol; 4-methyl-aminophenol; 4-amino-2-(aminomethyl)phenol; 4-amino-2-(hydroxymethyl)-phenol; 4-amino-2-fluorophenol; 4-amino-2-[(2-hydroxyethyl)-amino)methyl-phenol; 4-amino-2-methylphenol; 4-amino-2-(methoxymethyl)phenol; 4-amino-2-(2-hydroxyethyl)phenol; 5-aminosalicylic acid; 2,5-diaminopyridine; 2,4,5,6-tetraaminopyrimidine; 2,5,6-triamino-4-(1H)-pyrimidone; 4,5-diamino-1-(2-hydroxyethyl)-1H-pyrazole; 4,5-diamino-1-(1-methylethyl)-1H-pyrazole; 4,5-diamino-1-[(4-methylphenyl)methyl]-1H-pyrazole; 1-[(4-chlorophenyl)methyl]-4,5-diamino-1H-pyrazole; 4,5-diamino-1-methyl-1H-pyrazole; 2-aminophenol; 2-amino-6-methylphenol; 2-amino-5-methylphenol and 2,4-dihydroxyphenol.

8. The composition as defined in claim 5, containing from 0.005 to 20 percent by weight of each of said at least one developer and said at least one coupler.

9. The composition as defined in claim 5, further comprising at least one direct dye compound.

10. The composition as defined in claim 5, consisting of a hair colorant.

11. The composition as defined in claim 5, wherein said N-benzyl-m-phenylenediamine derivative is selected from the group consisting of 4-amino-2-{[5-amino-2-(2-hydroxyethoxy)-phenylamino]methyl}-phenol, 4-amino-2-{[5-amino-4-(2-hydroxyethoxy)-phenylamino]methyl}-phenol, 2-[4-amino-2-(3,5-diamino-benzylamino)phenoxy]ethanol, 2-[4-amino-2-(4-dimethylamino-benzylamino)-phenoxy]-ethanol, 2-[4-amino-2-(4-methoxy-benzylamino)-phenoxy]-ethanol, 2-(4-amino-2-benzyl-aminophenoxy)-ethanol, 2-{4-amino-2-[(pyridin-2-ylmethyl)-amino]-phenoxy}-ethanol, 2-[4-amino-2-(2-methoxy-benzylamino)-phenoxy]-ethanol, 2-[4-amino-2-(2-amino-benzyl-amino)phenoxy]-ethanol, 3-[(4-{[5-amino-2-(2-hydroxy-ethoxy)-phenylamino]-methyl}-phenyl)-(2-cyanoethyl)-amino]-propionitrile, 2-[4-amino-2-(4-amino-benzylamino)-phenoxy]ethanol, 2-[(4-{[5-amino-2-(2-hydroxyethoxy)phenyl-amino]methyl}-phenyl)-(2-hydroxyethyl)amino]-ethanol, 2-{[5-amino-2-(2-hydroxyethoxy)-phenylamino]-methyl}-benzene-1,4-diol, 2-[4-amino-2-(4-nitrobenzylamino)-phenoxy]-ethanol, 2-[4-amino-2-(3-aminobenzylamino)-phenoxy]-ethanol, 2-(4-{[5-amino-2-(2-hydroxy-ethoxy)phenyl-amino]-methyl}-phenoxy)-ethanol, N-(4-{[5-amino-2-(2-hydroxyethoxy)-phenylamino]-methyl}-phenyl)-acetamide, 4-{[5-amino-2-(2-hydroxyethoxy)-phenylamino]methyl}-phenol, 3-{(5-amino-2-(2-hydroxyethoxy)-phenylamino]-methyl}-phenol, 2-{[5-amino-2-(2-hydroxy-ethoxy)-phenylamino]-methyl}-phenol, 4-{[5-amino-2-(2-hydroxyethoxy)-phenyl-amino]-methyl}-benzoic acid, 2-[4-amino-2-(2-morpholin-4-yl-benzylamino)-phenoxyethenol, 3-[4-amino-2-(3,5-diamino-benzylamino)phenoxy]-propanol, 3-[4-amino-2-(4-dimethylaminobenzylamino)-phenoxy]-propanol, 3-(4-amino-2-(4-methoxybenzylamino)-phenoxy]-propanol, 3-(4-amino-2-benzlamino-phenoxy)-propanol, 3-{4-amino-2-[(pyridin-2-ylmethyl)-amino]phenoxy}-propanol, 3-[4-amino-2-(2-methoxybenzylamino)phenoxy]-propanol, 3-[4-amino-2-(2-amino-benzylamino)phenoxy]-propanol, 3-[4-amino-2-(4-aminobenzyl-amino)-phenoxy]-propanol, 3-[(4-{[5-amino-2-(2-hydroxyethoxy)-phenylamino]-methyl}-phenyl)-(2-hydroxyethyl)amino]propanol, 3-[4-amino-2-(4-nitrobenzyl-amino)-phenoxy]-propanol, 3-[4-amino-2-(3-aminobenzylamino)-phenoxy]-propanol, 3-(4-{[5-amino-2-(2-hydroxyethoxy)phenylamino]-methyl}-phenoxy)-propanol, 4-{[5-amino-2-(3-hydroxypropoxy)phenylamino]-methyl}-phenol, 2-{[5-amino-2-(3-hydroxypropoxy)phenylamino]-methyl}-phenol, 2-{[5-amino-2-(3-hydroxypropoxy)-phenylamino]-methyl}-phenol, 3-[4-amino-2-(2-morpholin-4-yl-benzylamino)-phenoxy]- propanol, $N^3$-benzyl-1,3-diamino-4-(2-methoxyethoxy)-benzene, $N^3$-(3-aminobenzyl)-1,3-diamino-4-(2-methoxyethoxy)-benzene, $N^3$-(2-aminobenzyl)-1,3-diamino-4-(2-methoxyethoxy)-benzene, $N^3$-(4-aminobenzyl)-1,3-diamino-4-(2-methoxyethoxy)-benzene, 3-{[5-amino-2-(2-methoxy-ethoxy)-phenylamino]methyl}-phenol, 2-{[5-amino-2-(2-methoxyethoxy)-phenyl-amino]-methyl}phenol, 4-{[5-amino-2-(2-methoxy-ethoxy)-phenylamino]-methyl}-phenol, $N^3$-benzyl-1,3-diamino-4-methoxybenzene, $N^3$-(3-aminobenzyl-1,3-diamino-4-methoxybenzene, $N^3$-(2-amino-benzyl)-1,3-diamino-4-methoxy-benzene, $N^3$-(4-aminobenzyl)-1,3-diamino-4-methoxybenzene, 3-{[5-amino-2-methoxy-phenylamino]-methyl}-phenol, 2-{[5-amino-2-methoxy-phenylamino]-methyl}-phenol, 4-{[5-amino-2-methoxy-phenyl-amino]-methyl}-phenol, $N^3$-benzyl-1,3-diamino-4-fluorobenzene, $N^3$-(3-aminobenzyl)-1,3-diamino-4-fluorobenzene, $N^3$-(2-aminobenzyl)-1,3-diamino-4-fluorobenzene, $N^3$-(4-aminobenzyl)-1,3-diamino-4-fluorobenzene, 3-{[5-amino-2-fluoraphenylamino]-methyl}-phenol, 2-{[5-amino-2-fluorophenyl-amino]-methyl}-phenol, and 4-{[5-amino-2-fluorophenylamino]methyl}-phenol.

\* \* \* \* \*